US00PP15687P3

(12) United States Plant Patent
Stemkens

(10) Patent No.: US PP15,687 P3
(45) Date of Patent: Mar. 22, 2005

(54) ***VERBENA* PLANT NAMED 'DUPLENA'**

(50) Latin Name: *Verbena×hybrida*
Varietal Denomination: Duplena

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 70 days.

(21) Appl. No.: 10/342,699

(22) Filed: Jan. 15, 2003

(65) Prior Publication Data

US 2004/0139520 P1 Jul. 15, 2004

(51) Int. Cl.[7] ..... A01H 5/00
(52) U.S. Cl. ..... Plt./308
(58) Field of Search ..... Plt./308

*Primary Examiner*—Kent Bell
*Assistant Examiner*—Louanne Krawczewicz Myers
(74) *Attorney, Agent, or Firm*—Edouard G. Lebel

(57) ABSTRACT

A new and distinct variety of *Verbena* plant particularly distinguished by its lilac flowers, early flowering, and a spreading habit that is first semi-erect and later spreading.

1 Drawing Sheet

Botanical classification: *Verbena×hybrida.*
Varietal denomination: 'Duplena'.

BACKGROUND OF THE NEW PLANT

The present invention comprises a new distinct cultivar of *Verbena,* botanically known as *Verbena×hybrida.*

The new cultivar is propagated from cuttings resulting from the cross of 'X816-1' and 'X-816-2'. 'X816-1' is a violet flowering *Verbena* having a spreading habit. 'X816-1' is not commercially available and is not known by any synonyms. 'X816-2' is a pink flowering *Verbena* having a spreading habit. 'X816-2' is not commercially available and is not known by any synonyms. Neither 'X816-1' nor 'X816-2' has been patented.

As a result of this cross the present cultivar was created in 1998 in Enkhuizen, Netherlands and has been repeatedly asexually reproduced by cuttings in Enkhuizen, Netherlands and Sarrians, France over a three-year period. It has been found to retain its distinctive characteristics through successive propagations, and this novelty appears to be firmly fixed.

This new *Verbena* plant is an annual in most climatical zones in the US, only in zones 9 and 10 it is a perennial plant.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena.* The data which defines these characteristics were collected from asexual reproductions carried out in Enkhuizen, Netherlands. The plant history was taken on 14 weeks old plants, blossomed under natural light in a greenhouse and grown in a 10.5 cm container.

Color readings were taken in the greenhouse under ambient light. Color references are primarily to The R.H.S. Colour Chart of The Royal Horticultural Society of London.

Differences between the new cultivar 'Duplena,' its parents and a similar cultivar

| | 'Duplena' | 'X816-1' | 'X816-2' | 'Temari lilac' |
|---|---|---|---|---|
| Flower color | Light lilac | Violet | Pink | Deep lilac |
| Earliness | Early | Very early | Late | Late |
| Internode length | Short | Short | Long | Very long |
| Plant size | Medium | Compact | Big | Big |
| Seed set | No | No | Much | Abundant |

The commercial name of the most resembling variety is 'Temari lilac.' The patented name of this variety is 'Sunmaricos' and its U.S. Plant Pat. No. is 14,292.

The plant

Classification — botanical: *Verbena×hybrida*
Parentage:
*Female parent.*—A seedling named 'X816-1' is one of our seedlings from our Z-generation of plants bred in 1996.
*Pollen parent.*—A seedling named 'X816-2' is one of our seedlings from our Z-generation of plants bred in 1996.
Growth habit: Spreading
Plant height: 14–20 cm
Spreading area of plant: 35–65 cm
Growth rate: Hanging and vigorous
Strength: Resistant to hot and cold weather
Branching character: Freely branching and lateral branching at every node
Blooming period: From April until November

The stem

Diameter: 2.5–3 mm
Length: 8–12 cm
Shape: Tetragonal
Color: Deep green 137D

Anthocyanin pigmentation: Present, color 180D
Length of internode: 20–40 mm, depending on the light where the plant is propagated
Pubescence: Pubescence is present
Length lateral branches: 17–28 cm The foliage Phyllotaxis: Opposite
Shape of blade: Broadly ovate
Texture:
*Upper side.*—Pubescent.
*Lower side.*—Pubescent.
Venation: Pinnate
Leaf margin: Simple incised
Leaf base: Shortly attenuate
Leaf apex: Acute
Length: 25–40 mm
Width: 18–30 mm
Depth of incision: 2–4 mm
Color:
*Upper side.*—Dark green 137C.
*Lower side.*—Light green 138A.
Pubescence: Some pubescence is present
Length of leaf stem: 5–12 mm
Petiole surface structure: Slightly pubescent
Petiole diameter: 2–3 mm
Petiole coloration: 141C The bud Peduncle length: 30–60 mm, depending on season
Peduncle diameter: 2–3 mm
Peduncle color: 138A
Size of the bud:
*Length.*—8–12 mm.
*Diameter.*—2 mm.
Shape: Elongated and ovate
Color: Medium green 137D
Sepals:
*Color* (*upper side*).—Light green 138B.
*Color* (*lower side*).—138C.
*Form.*—Upright.
*Number.*—5, fused.
*Length.*—6–7 mm.
*Width.*—2 mm.
*Shape.*—Elongated.
*Apex.*—Apiculate.
*Base.*—Fused.
*Margin.*—Entire.

The flower

Facing direction: Upward
Outward curvature of petal: Slightly curved
Flower diameter: 18–24 mm
Flower height: 16–18 mm
Flower tube length: 14–16 mm
Flower throat diameter: 2 mm
Borne: In a cluster
Form: Salverform; sessile on terminal spikes
Petal color:
*Upper side.*—Lilac N81A.
*Lower side.*—Lilac N81C.
Eye: A very small (1 mm) whitish Eye (155C) is present Typically three out of the five petals exhibit this whitish coloration on the upper side of them
Overlapping of the petals: Separate
Number of petals: Gamopetalous, five lobed
Shape of the petals: Each petal is obcordate
Petal apex: Emarginate
Petal base: Fused
Petal margin: Entire
Petal surface texture: Smooth
Size of the petal:
*Length.*—6–8 mm.
*Width.*—6–8 mm.
Inflorescence:
*Length.*—25–35 mm.
*Diameter.*—30–40 mm.
Calyx length: 8–10 mm
Calyx diameter: 2–3 mm
Anthocyanin pigmentation of calyx limb: Absent.
Color of the calyx: Light green 138C (outside surface)
No. of flowers per inflorescence: 20–25
Fragrance: A very light rosy fragrance occurs
Bloom time of one inflorescence: New florets continue to open over a period of 14 days
Lastingness of one flower: 2–5 days The reproductive organs Androecium:
*Stamen quantity.*—Four.
*Anther shape.*—Ovoid.
*Anther length.*—1 mm.
*Anther color.*—144D.
*Amount of pollen.*—Scarce pollen.
*Pollen color.*—145D.
Gynoecium:
*Pistil quantity.*—1.
*Stigma shape.*—Bi-lobed.
*Pistil length.*—1.8–2.2 mm.
*Stigma color.*—144C.
*Style length.*—1.4–1.8 cm.
*Style color.*—144D.
*Ovary color.*—144C.

The seed

Seedset: No seedset has been observed

The roots

Type of roots: Fibrous. Roots starts to grown on every part of the stem That contacts the soil, so not only at the nodes.
Physiological and ecological characteristics: Good tolerance to heat and cold. Strong resistance to pests and diseases, particularly powdery mildew.

What is claimed is:

1. A new and distinct cultivar of *Verbena* plant named 'Duplena', as illustrated and described.

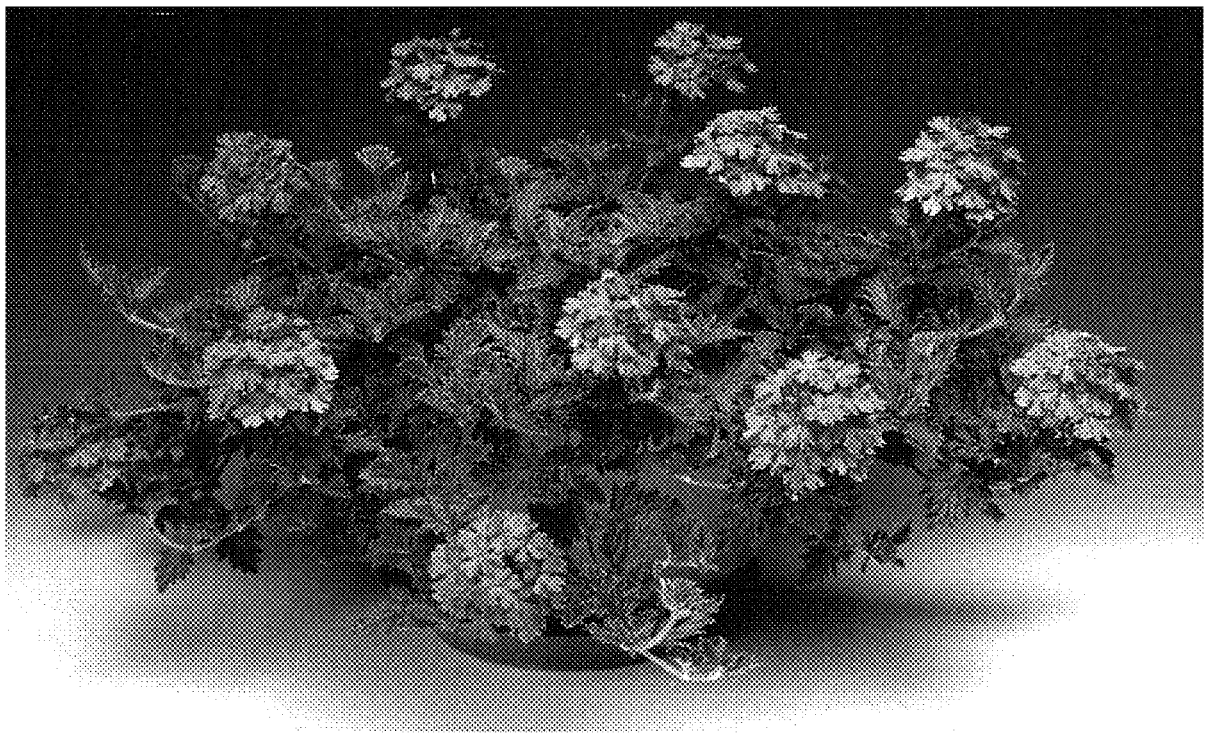

* * * * *